(12) United States Patent
Bonanno et al.

(10) Patent No.: US 11,266,815 B1
(45) Date of Patent: Mar. 8, 2022

(54) CLOSED-SYSTEM BLADDER DRUG ADMINISTRATION CATHETER AND METHODS FOR ADMINISTERING DRUGS IN A CLOSED SYSTEM

(71) Applicant: GENIUS MEDICAL SYSTEMS, LLC, Pembroke Pines, FL (US)

(72) Inventors: Milena Bonanno, Weston, FL (US); Charles Bonanno, Davie, FL (US)

(73) Assignee: GENIUS MEDICAL SYSTEMS, LLC, Pembroke Pines, FL (US)

( * ) Notice: Subject to any disclaimer, the term of this patent is extended or adjusted under 35 U.S.C. 154(b) by 0 days.

(21) Appl. No.: 17/324,780

(22) Filed: May 19, 2021

(51) Int. Cl.
  *A61M 25/10* (2013.01)
  *A61M 39/22* (2006.01)
  (Continued)

(52) U.S. Cl.
  CPC ............ *A61M 25/10* (2013.01); *A61K 31/407* (2013.01); *A61K 31/7068* (2013.01); *A61M 1/82* (2021.05);
  (Continued)

(58) Field of Classification Search
  CPC .......... A61M 25/10; A61M 2039/1077; A61M 2210/1085; A61M 2210/1089;
  (Continued)

(56) References Cited

U.S. PATENT DOCUMENTS

| | | |
|---|---|---|
| 7,998,106 B2 | 8/2011 | Thorne, Jr. et al. |
| 8,597,232 B2 | 12/2013 | Lev et al. |

(Continued)

FOREIGN PATENT DOCUMENTS

| | | |
|---|---|---|
| CN | 202437789 U | 9/2012 |
| CN | 209154693 U | 7/2019 |
| CN | 110975067 A | 4/2020 |

OTHER PUBLICATIONS

Hazardous Drugs—Handling in Healthcare Settings; usp.org, revision bulletin, posting date May 31, 2019 (updated Sep. 27, 2019; Official Dec. 1, 2019, (20 pages).
Equashield—Closed System Drug Transfer Device (16 pages).

*Primary Examiner* — Amber R Stiles
(74) *Attorney, Agent, or Firm* — Gregory L. Mayback; Dickinson Wright PLLC

(57) ABSTRACT

A closed-system, drug administering catheter assembly includes a transfer adapter, a stopcock, a medicament injector containing chemotherapy medicament, a medicament pressure reservoir, and a urethral balloon catheter comprising a drain lumen and a distal tip, all connected together in a closed-system. The medicament injector is configured to inject the chemotherapy medicament through the stopcock, the drain lumen, and into an environment of the distal tip within a patient's organ without leakage of the chemotherapy medicament from the patient into an environment of the patient. The medicament pressure reservoir is configured to store negative pressure that withdraws from the organ used chemotherapy medicament through the drain lumen and the stopcock and holds the used chemotherapy medicament in the medicament pressure reservoir without leakage of the used chemotherapy medicament into the environment of the patient.

43 Claims, 6 Drawing Sheets

(51) Int. Cl.
*A61M 1/00* (2006.01)
*A61K 31/7068* (2006.01)
*A61K 31/407* (2006.01)
*G06Q 40/08* (2012.01)
*G16H 40/20* (2018.01)
*A61M 39/10* (2006.01)
*G06Q 50/26* (2012.01)
*G16H 20/17* (2018.01)

(52) U.S. Cl.
CPC ............ *A61M 39/10* (2013.01); *A61M 39/22* (2013.01); *A61M 39/223* (2013.01); *G06Q 40/08* (2013.01); *G16H 40/20* (2018.01); *A61M 2039/1077* (2013.01); *A61M 2039/229* (2013.01); *A61M 2210/1085* (2013.01); *A61M 2210/1089* (2013.01); *G06Q 50/26* (2013.01); *G16H 20/17* (2018.01)

(58) Field of Classification Search
CPC ...... A61M 39/223; A61M 1/82; A61M 39/22; A61M 39/10; A61M 2039/229; A61K 31/7068; A61K 31/407; G06Q 40/08; G06Q 50/26; G16H 40/20; G16H 20/17
See application file for complete search history.

(56) References Cited

U.S. PATENT DOCUMENTS

| | | | |
|---|---|---|---|
| 2004/0171979 A1* | 9/2004 | O'Neil | A61M 31/00 604/19 |
| 2006/0224105 A1 | 10/2006 | Thorne, Jr. et al. | |
| 2011/0301539 A1 | 12/2011 | Rickard | |
| 2013/0131609 A1 | 5/2013 | Kawashinma | |

* cited by examiner

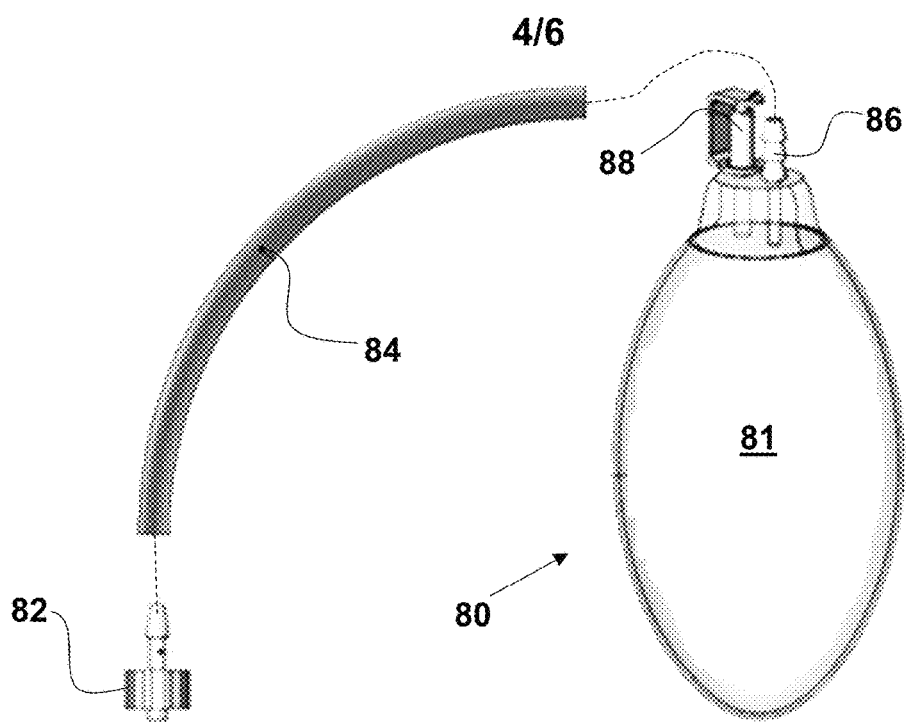
FIG. 13
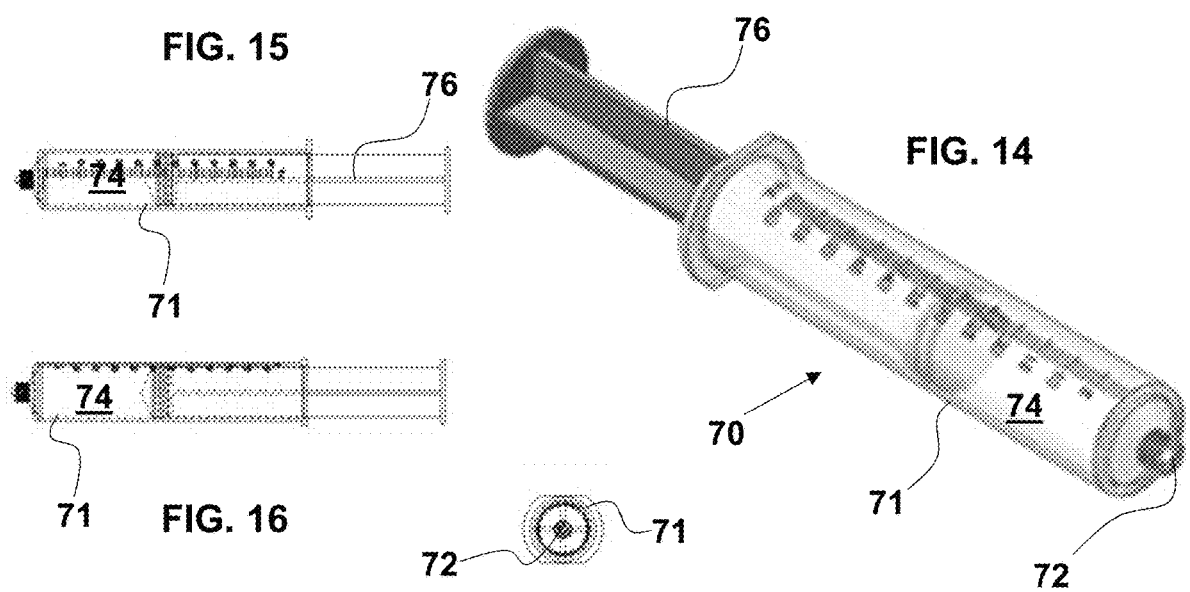
FIG. 15
FIG. 14
FIG. 16
FIG. 17

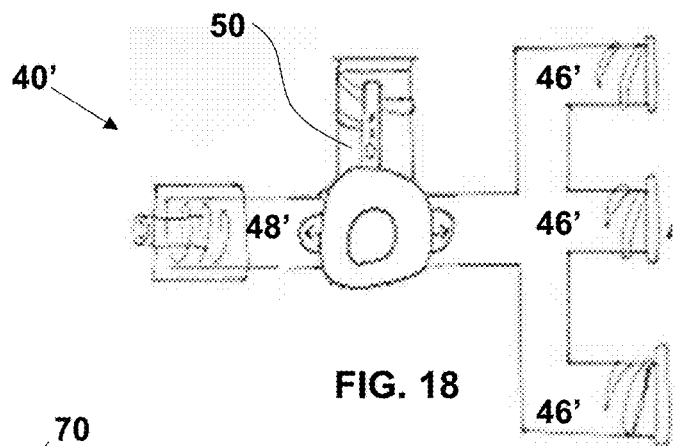
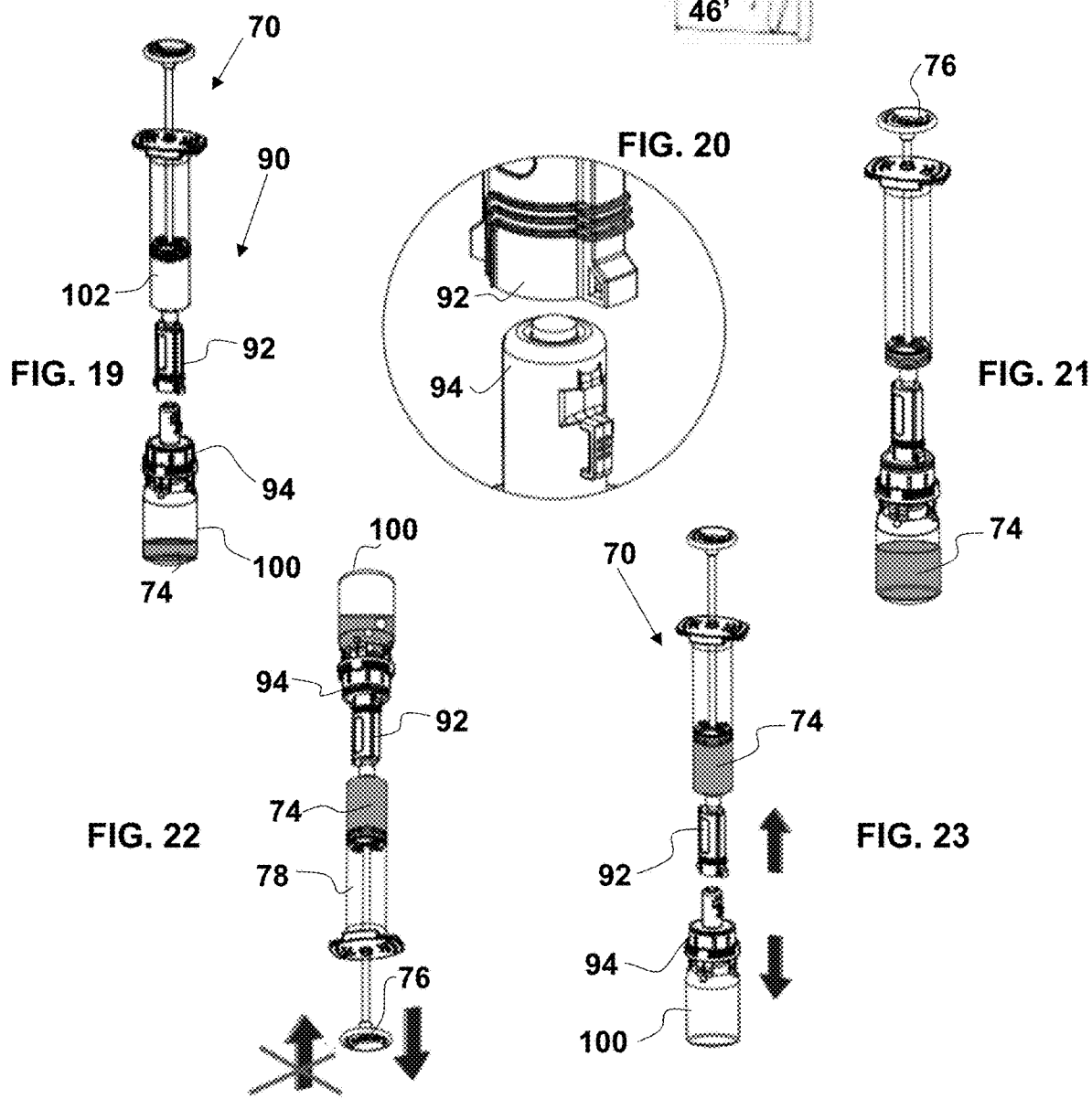

CLOSED-SYSTEM BLADDER DRUG ADMINISTRATION CATHETER AND METHODS FOR ADMINISTERING DRUGS IN A CLOSED SYSTEM

STATEMENT REGARDING FEDERALLY SPONSORED RESEARCH OR DEVELOPMENT

Not Applicable

FIELD OF THE INVENTION

The present systems, apparatuses, and methods lie in the field of closed-system drug delivery. The present disclosure relates to a closed-system, drug administering catheter and catheter system for bladder chemotherapy treatment and methods for administering drugs to the interior of structures, such as the bladder, without exposing the drugs to the environment outside the structure.

BACKGROUND OF THE INVENTION

Bladder cancer plagues hundreds of thousands of people every year in the United States. In 2017 alone, the NIH estimated that 712,614 people were living with bladder cancer, 90% of which were over the age of 55 (ASCO), and most of which are men. Among these statistics, the keyword "living" is significant. Unlike many cancers, bladder cancer is often detected early enough to treat it successfully and keep it from coming back in the future. In 2020, the NIH expected that an additional 81,400 adults would be diagnosed, over half of which would be diagnosed at the early stage with Non-Muscle Invasive Bladder Cancer (NMIBC). NMIBC is the least severe stage (stage 0), followed by Minimally Invasive Bladder Cancer (stage 1), both of which have not spread around the body and are completely limited to the inner lining of the bladder. This means that well over half of new bladder cancer patients can be treated solely with what is called Intravesical Chemotherapy (or Immunotherapy depending on the drug administered). Intravesical therapies are administered directly to the cancerous area, which reduces or eliminates the systemic side effects associated with standard chemotherapies like hair loss, nausea, vomiting, weakness, etc. Even in the cases of more advanced bladder cancers that have invaded the muscle wall, spread, and/or formed tumors, intravesical treatment is often used after transurethral resection of bladder tumors (TURBT) or in combination with standard chemotherapy treatments to treat and prevent prophylactically the reoccurrence of tumors at the source. With such a large population of bladder cancer patients benefitting from this kind of intravesical therapy, there is already a common procedure in place for best practices for administration of medication.

With intravesical therapy, the doctor places a liquid drug into the cavity of the bladder with a soft catheter inserted through the urethra. The drug stays in the bladder for a given amount of time, for example, between approximately one to four hours, in particular, between approximately one-and-a-half to two hours, and, in many instances about two hours. In this way, the drug affects only the cells lining the inside of the bladder and, by not being administered systemically, it does not introduce the adverse effects on other parts of the body that other treatments routinely exhibit. At termination of the treatment, the drugs are drained into a secure receptacle or reservoir and, depending on the surgeon's practice, the bladder is also flushed after drainage with the flush also drained into the receptacle.

The reason for needing this secure receptacle is because chemotherapy drugs used for treating bladder cancer are hazardous to humans. Therefore, it is important to keep the drugs contained at all times, except when they are actually administered into the bladder of the patient. Both mitomycin and gemcitabine are examples of bladder chemotherapy drugs having this disadvantageous property. A single, closed system that contains these drugs at all times from before the procedure until ultimate disposal is not available at the present time; current methodologies require transfer by the medical staff or surgeon at least at one point during the procedure.

EdgePharma offers compounded Gemcitabine, bladder-instillation syringe kits that include a 1 g/50 mL pre-filled unit-dose syringe of Gemcitabine, a separate, closed-system transfer device (CSTD), and catheter tip. The Gemcitabine arrives at the purchaser in a ready-to-administer state.

EdgePharma also offers compounded Mitomycin, bladder-instillation syringe kits that include a 40 mg/40 mL pre-filled unit-dose syringe of Mitomycin, a separate CSTD, and catheter tip. These devices may be found on the Internet at:

https://edgepharma.com/products/urology/gemcitabine-bladder-instillation/
https://edgepharma.com/products/urology/mitomycin-bladder-instillation/

The only material difference between these two kits is the drug they use. Importantly, these systems have significant disadvantages. Primarily, during drug administration, the system is not closed. Specific components need to be attached and/or added such as, for example, a luer-lock catheter, a syringe, catheter tubing, and a closed-system transfer device. Handling of waste after the drug treatment during the removal of the drug from the bladder is also not a closed system. These systems simply do not provide a single closed path from the beginning of the procedure until they are ready for proper hazardous waste disposal.

China Patent Document No. CN209154693U, titled "A kind of bladder treatment lavation equipment," describes equipment with a connector, a connecting tube, a triple valve, a positive pressure connector, a syringe, and a catheter. One end of the connector is connected to the connecting tube and the other end of the connector is connected to the catheter. The other end of the connecting tube is connected to the triple valve. The positive pressure connector is fixed to the three-way valve. This equipment does not provide a single, closed path.

United States Patent Publication No. 2013/0131609 to Kawashima describes a three-way stopcock unit that is used for directly administering a nutritional composition to the stomach of a patient. It is not part of a system and is merely a stopcock.

Current intravesical chemotherapy treatments have a few steps. A relatively standard physical examination takes place prior to beginning intravesical therapy. The examination includes patient identification, confirmation of physician order to treat, assessment of vital signs and general well-being, assessment of ability to retain fluid in the bladder for necessary treatment time, urine analysis, and, finally, a perineal inspection including pain assessment (bladder, back, and pelvic). Once the patient is cleared from this examination, they are asked to void their bladder (the bladder can also be drained through a Foley catheter if the patient is unable to do so). The procedure 1000 can then begin. From this point, the steps of the procedure 1000 are straightforward and detailed in FIG. 1. A sterile catheterization is performed pursuant to surgeon/clinic/unit protocol in step 1010. The surgeon ensures that the bladder is drained in step 1020. In step 1030, a catheter tipped syringe containing the treatment is inserted into the catheter with a safety adapter to prevent leakage during attachment to the catheter. In step 1040, the medication is slowly injected while assessing the patient's pain level. In step 1050, the syringe is removed and, at the same time, the catheter is squeezed closed and/or plugged (e.g., with a hemostat) so that the chemotherapy is held in the bladder for the specified treatment time (usually one to two hours). During the treatment period, in step 1060, the patient could be asked to roll, from left to right and/or to reposition every fifteen minutes or so to ensure that the drug coats the entire inner lining of the bladder. After the desired dwell time, in step 1070, the physician drains the medication out of the bladder through the catheter and into a urinary drainage bag, and the bag is disposed of properly for medicines having hazardous properties. Finally, in step 1080, the physician repeats a perineal inspection, cleans any leaks, assesses the patient for pain again, and the medical staff schedules a follow-up appointment.

The current procedure 1000 takes place in a hospital setting, due to the number of controls put in place for safe administration of the hazardous chemotherapy drug. Personal protective equipment (PPE) like chemotherapy-protective gloves, eye gear, and facemasks, as well as engineering controls for the transfer of the drug from vial to syringe in a biological safety cabinet are just the beginning of the safe work practices that are required when administering hazardous chemo- and immune-therapies. These practices are time-consuming and costly. Health regulations also require a separate, expensive, biohazardous or chemotherapy waste container for disposal and transportation of this waste. These few controls (there are more) make a seemingly simple procedure very complex. Thus, the procedure is required to be performed in a hospital setting. In actuality, Urologists are capable of doing the entire procedure themselves in their own offices or outpatient clinics but are forced to send their patients to a hospital because the current systems do not protect and secure the hazardous drug adequately.

Most outpatient urology clinics are not currently equipped with a closed-system device or hood to transfer the drug from the supplier's vial to a usable syringe, and then from the syringe to the catheter, and, subsequent to use, back out of the body safely, without harmful exposure to patient or physician or others in the immediate vicinity. Clinics do not normally have biological safety cabinets or negative pressure rooms to contain safely the hazardous drug or its equally dangerous fumes. In addition, there is now a higher focus on hazardous drug compounding in USP Chapter 800 "Hazardous Drugs—Handling in Healthcare Settings" that virtually prohibits doctors' offices and outpatient facilities from mixing their own drug solutions because there are extremely specific lab-like engineering controls required to mix safely chemotherapy drugs. See https://www.uspnf.com/sites/default/files/usp_pdf/EN/USPNF/revisions/gc-800-rb-notice-20190531.pdf. This is a positive change because it protects employees and patients from careless handling or accidental exposure. However, most offices have not been set up this way, and it creates a massive expense to an office to literally renovate and upgrade their facilities to house an entire lab set up. Consequently, the current solution requires sending patients to hospitals for these procedures, as they are already properly equipped for the mixing and administration of this therapy with current processes.

There are many problems associated with requiring hospital settings for these treatments, however. First, it is much more expensive to the patient and to the healthcare industry in general. Further, it is less profitable for the urologist to have these simple procedures limited to a hospital room. Next, it causes unnecessary inconvenience to patients, who have to spend a day in the hospital for something that could be/should be done in an outpatient setting in just a few hours. If the urologist could perform the procedure in their own office, they could bill the health insurance for a procedure, making this process more lucrative for the doctor while reducing overall cost to the insurer and/or the patient and/or the industry. In such a desirable situation, patients would not need to go to the hospital. They just would travel to their urologist's office as a regular appointment. Their comfort and convenience axiomatically increases. Significantly, there is a decrease in the fear and trepidation for the procedure. However, these benefits have not been achievable with current resources and technologies.

Thus, a need exists to overcome the problems with the prior art systems, designs, and processes as discussed above.

SUMMARY OF THE INVENTION

The systems, apparatuses, and methods described provide a closed-system, drug administering catheter for bladder chemotherapy treatment and methods for administering drugs to the interior of structures, such as the bladder, without exposing the drugs to the environment outside the structure that overcome the hereinafore-mentioned disadvantages of the heretofore-known devices and methods of this general type and that provide such features by retaining therein the hazardous drugs before being injected into the bladder through a urinary catheter and then retaining the drugs in a reservoir, connected to the same catheter, that creates suction to remove the same drugs from the bladder, all the while being a safe and secure closed system.

The instant GEnito-urinary Novel Intra-Urethral System, referred to as GENIUS™, is an entirely closed-system device, including a pre-filled syringe, with attachments for administration of drug and drainage of waste fluid, all without requiring disassembly of the device. This means that, from start to finish, the drug being utilized never has an opportunity to be exposed to the environment, or to leak or escape out of the device/system. The greatest precautions and controls that need to be in place for the instant systems, apparatuses, and methods to be employed are a sterile catheterization and PPE for the health team (masks, eyewear, and chemo gloves), which is the same as all existing recommended procedures. However, all controls for the safe transfer of the hazardous fluids (e.g., the chemotherapy drug) are no longer needed and, therefore, rendered superfluous. Where the hazardous liquid is the chemotherapy drug, the fluid comes pre-filled in a secure syringe, eliminating any need for a biological safety cabinet (e.g., hood). Where the hazardous powder is the chemotherapy drug, the powder comes pre-filled in a secure receptacle that attaches to a hydrating syringe assembly and, upon hydration, transfers the now hazardous drug liquid into the secure syringe of the closed-system, thereby eliminating any need for the biological safety cabinet. The closed-system device for transfer from the syringe to the catheter is already attached between the syringe and the balloon catheter (both included) upon delivery of the system to the physician. The catheter can be detached for easier insertion into the patient without having any association or disturbance of the drug delivery subassembly, including the hazardous fluid contained within the syringe. In other words, even with the catheter removed, the system keeps the chemotherapy drug contained and protected from exposure to the patient, to the doctor and other medical staff, and to the environment surrounding the patient due to its closed-system transfer structure. An office-independent waste reservoir is provided and connected to receive the final waste flow of fluid, which comprises the path out of the patient's body and into the waste reservoir. This waste reservoir is a self-contained and fortified storage unit that, when filled with the hazardous fluid, resists tampering or breakage and holds the fluid securely until proper disposal can be made. One exemplary embodiment of the waste reservoir is a surgical drain bulb. Another exemplary embodiment is a catheter drainage bag that is fortified by being of a material resistant to the properties of the used drug. One exemplary material is Di(2-ethylhexyl)phthalate (DEHP).

A three-way stopcock acts as a "traffic light" at an intersection of the system. A position of the stopcock determines direction of fluid flow at each stage of the procedure. The procedure begins with the stopcock in a closed position while the catheter is being inserted. In a next step, the stopcock is opened to permit flow between the syringe and the internal lumen of the urinary catheter (which can be referred to as the drain lumen 11). In this step, the urologist injects medication from the syringe through the stopcock and catheter and into the bladder. Next, the stopcock is closed to prevent liquid from travelling out through the lumen of the catheter and into the system. In this stage, the medication is held within the bladder for a prescribed period. Alternatively, or additionally, a plunger of the syringe can be locked to prevent any fluid flow through the system regardless of a position of the stopcock. In a further step, the stopcock is turned to a final position in which flow is permitted to occur between the bladder and the waste reservoir through the catheter. In one exemplary embodiment where the waste reservoir is of a material that can stand to be at negative pressure for years, the waste reservoir is pressurized negatively in the packaged state. In another exemplary embodiment, the waste reservoir is at a steady or rest state in the package delivered to the physician/clinic. Before or during the procedure, the physician transitions the waste reservoir from its steady, unpressurized state to a negative pressure state. For example, if the waste reservoir is a surgical drain bulb, just before or during the procedure, the physician squeezes the bulb to evacuate all of the air therein while the bulb's entry port is plugged, thereby creating negative pressure in the bulb and storing potential energy in the bulb to be in a ready state to draw out most or all of the fluid in the bladder when the interior of the bulb is allowed to fluidically connect with the interior of the bladder. This low (and, therefore, sufficient but gentle) vacuum pressure applied to the interior cavity of the bladder safely assists the patient in voiding the medication at termination of the procedure. After deflating the catheter balloon, the urologist removes the catheter from the patient's body, wiping any leaks quickly, and disposing of the entire Genius device (and any contaminated materials) in a chemotherapy disposal bag for safe removal in a hazardous waste container or other secure system. An exemplary physician procedure can include a rinsing step to inject saline or other fluid into the bladder after drainage of the medication with the subsequent drainage of the rinsing fluid into the waste reservoir.

It is noted that, if the patient needs help in voiding their bladder prior to the procedure, after insertion of the catheter into the patient's bladder, but before attachment of the catheter to the drug delivery subassembly, the catheter can be easily connected to a standard Foley bag. In this state, the catheter can be used, as a typical Foley catheter, to drain the bladder. Once complete, the Foley bag can be detached and disposed of pursuant to clinic/unit protocol, and the catheter can be reattached to the drug delivery subassembly.

With the foregoing and other objects in view, there is provided, a closed-system, drug administering catheter assembly comprises a transfer adapter, a stopcock, a medicament injector containing chemotherapy medicament, a medicament pressure reservoir, and a urethral balloon catheter comprising a drain lumen and a distal tip, all connected together in a closed-system, the medicament injector being configured to inject the chemotherapy medicament through the stopcock, the drain lumen, and into an environment of the distal tip within a patient's organ without leakage of the chemotherapy medicament from the patient into an environment of the patient, and the medicament pressure reservoir being configured to store negative pressure that withdraws from the organ used chemotherapy medicament through the drain lumen and the stopcock and holds the used chemotherapy medicament in the medicament pressure reservoir without leakage of the used chemotherapy medicament into the environment of the patient.

With the objects in view, there is also provided a closed-system, drug administering catheter assembly comprises a urethral balloon catheter comprising a drain lumen and a distal tip, a transfer adapter fluidically connected to the drain lumen, a stopcock fluidically connected to the transfer adapter, a medicament injector fluidically connected to the stopcock, a medicament pressure reservoir fluidically connected to the stopcock, and the transfer adapter, the stopcock, the medicament injector, the medicament pressure reservoir, and the balloon catheter connected together in a closed-system such that hazardous liquid chemotherapy medicament in the medicament injector is configured to be injected through the stopcock, the drain lumen, and into an environment of the distal tip within a patient's human bladder, left in the bladder for a given amount of time, and then withdrawn from the bladder through the drain lumen and the stopcock and into the medicament pressure reservoir by negative pressure stored in the medicament pressure reservoir, without leakage of the chemotherapy medicament from the patient into an environment of the patient. In accordance with another feature, In accordance with a further feature, the organ is a human bladder.

In accordance with an added feature, the transfer adapter comprises a distal connector comprising a distal orifice, a proximal connector comprising a proximal orifice, and an intermediate pressure-equalization valve fluidically connecting the distal orifice to the proximal orifice and configured to equalize pressure across the transfer adapter without leakage of liquid therein.

In accordance with an additional feature, the stopcock comprises an introductory flow state that permits fluidic flow between the medicament injector and the organ through the drain lumen, a closed state that substantially prevents liquid from travelling through the stopcock, and a drainage flow state that permits fluidic flow between organ and the pressure reservoir through the drain lumen.

In accordance with yet another feature, the stopcock is a three-way stopcock valve.

In accordance with yet a further feature, the stopcock comprises a hollow first connector comprising a first internal lumen, a hollow second connector comprising a second internal lumen, a hollow third connector comprising a third internal lumen, a body defining an interior plenum fluidically connected to the first, second, and third internal lumens and a diverter orifice, and a diverter rotatably attached to the body in the diverter orifice 52 and fluid-tightly sealed therein, the diverter configured to rotate and, thereby, fluidically connect or disconnect any number of the first, second, and third internal lumens.

In accordance with yet an added feature, the first connector is connected to the transfer adapter, the second connector is connected to the medicament injector, and the third connector is connected to the pressure reservoir.

In accordance with yet an additional feature, the diverter comprises an administration state in which the internal lumens of the first and second connectors are fluidically connected to one another to permit medicament from the medicament injector to enter the second connector and exit through the first connector and a drainage state in which the internal lumens of the first and third connector are fluidically connected to one another to permit fluid within the catheter drain lumen and the environment surrounding the distal tip to be drawn out from the environment 2, through the catheter, through the third connector, and into the pressure reservoir.

In accordance with again another feature, the diverter comprises a handle shaped to permit a user to turn the diverter between positions within the body and, thereby, fluidically connect or disconnect any number of the first, second, and third internal lumens.

In accordance with again a further feature, the medicament injector has a lock that prevents fluid flow through independent of a position of the stopcock.

In accordance with again an added feature, the chemotherapy medicament is hazardous liquid chemotherapy medicament.

In accordance with again an additional feature, the chemotherapy medicament is at least one of mitomycin and gemcitabine.

In accordance with still another feature, the chemotherapy medicament is first stored in a solid form and is then reconstituted in the medicament injector.

In accordance with still a further feature, the pressure reservoir is of a fortified material substantially impervious to the chemotherapy medicament.

In accordance with still an added feature, the material is at least one of di(2-ethylhexyl) phthalate (DEHP), dioctyl phthalate (DOP), and bis(2-ethylhexyl) phthalate (BEHP).

In accordance with still an additional feature, the pressure reservoir is a surgical drain bulb.

In accordance with a further feature, the negative pressure is created by a compression of the drain bulb.

In accordance with an added feature, the pressure reservoir is configured to hold a level of negative pressure for a given amount of time at least as long as a chemotherapy treatment procedure and to store the chemotherapy medicament after completing the chemotherapy treatment procedure and at least up until ultimate disposal of the used chemotherapy medicament.

In accordance with an additional feature, the balloon catheter comprises a proximal medicament port fluidically connected to the drain lumen, the transfer adapter comprises a distal connector comprising a distal orifice, a proximal connector comprising a proximal orifice, and an intermediate pressure-equalization valve fluidically connecting the distal orifice to the proximal orifice and configured to equalize pressure across the transfer adapter, the stopcock comprises a body defining a plenum, a first connector fluidically connected to the proximal connector of the transfer adapter, a second connector, a third connector, and a central body disposed in the plenum and configured to selectively connect at least one of the second and third connectors to the first connector, the medicament injector is filled with the chemotherapy medicament, comprises a distal medicament output fluidically connected to the second connector and is configured to inject the medicament through the stopcock, the drain lumen and into an environment of the distal tip, the medicament pressure reservoir comprises a reservoir input fluidically connected to the third connector and a body defining an interior fluidically connected to the reservoir input and configured to exert a negative pressure upon the third connector such that, responsive to fluidically connecting the drain lumen to the third connector through the stopcock, the negative pressure in the interior draws fluid in the environment of the distal tip through the drain lumen, through the transfer device, and into the interior of the pressure reservoir, and the catheter, the transfer adapter, the stopcock, the medicament injector, and the pressure reservoir together comprise a disposable closed-system responsive to being connected together with the medicament in the medicament injector.

In accordance with yet another feature, the closed-system of the transfer adapter, the stopcock, the medicament injector, the chemotherapy medicament, the medicament pressure reservoir, and the urethral balloon catheter is disposable.

In accordance with yet a further feature, the closed-system of the transfer adapter, the stopcock, the medicament injector, the chemotherapy medicament, the medicament pressure reservoir, and the urethral balloon catheter is billable under at least two separate standardized insurance processes.

In accordance with a concomitant feature, the closed-system product is billable by a provider under a commercial medical plan or Medicare (Part B) using a J code submission and by a pharmacy provider dispensing the closed-system product using the Pharmacy Benefit Manager (PBM) commercial or Part D insurance for a drug component having an NDC in addition to the medicament accompanying with the closed-system product.

Although the systems, apparatuses, and methods are illustrated and described herein as embodied in a closed-system, drug administering catheter for bladder chemotherapy treatment and methods for administering drugs to the interior of structures, such as the bladder, without exposing the drugs to the environment outside the structure, it is, nevertheless, not intended to be limited to the details shown because various modifications and structural changes may be made therein without departing from the spirit of the invention and within the scope and range of equivalents of the claims. Additionally, well-known elements of exemplary embodiments will not be described in detail or will be omitted so as not to obscure the relevant details of the systems, apparatuses, and methods.

Additional advantages and other features characteristic of the systems, apparatuses, and methods will be set forth in the detailed description that follows and may be apparent from the detailed description or may be learned by practice of exemplary embodiments. Still other advantages of the systems, apparatuses, and methods may be realized by any of the instrumentalities, methods, or combinations particularly pointed out in the claims.

Other features that are considered as characteristic for the systems, apparatuses, and methods are set forth in the appended claims. As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one of ordinary skill in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the systems, apparatuses, and methods of the invention that are regarded as novel, it is believed that the systems, apparatuses, and methods will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the systems, apparatuses, and methods. Advantages of embodiments of the systems, apparatuses, and methods will be apparent from the following detailed description of the exemplary embodiments thereof, which description should be considered in conjunction with the accompanying drawings in which:

FIG. 13 is an exploded perspective view of an exemplary embodiment of a medicament pressure reservoir sub-assembly of the system of FIG. 2;

FIG. 14 is a perspective and partially transparent view of an exemplary embodiment of a medicament injector of the system of FIG. 2;

FIG. 15 is a side elevational and partially transparent view of the medicament injector of FIG. 14;

FIG. 16 is a side elevational and partially transparent view of the medicament injector of FIG. 15 rotated about the longitudinal axis;

FIG. 17 is a top plan and partially transparent view of the medicament injector of FIG. 14;

FIG. 18 is a side elevational view of an exemplary embodiment of a W-connector;

FIG. 19 is a perspective view of an exemplary embodiment of a solid medicament storage vial and a medicament reconstitution device unconnected from one another;

FIG. 20 is an enlarged, fragmentary, perspective view of a portion of the vial and device of FIG. 19;

FIG. 21 is a perspective view of the medicament storage vial and reconstitution device of FIG. 19 connected to one another;

FIG. 22 is a perspective view of the medicament storage vial and reconstitution device of FIG. 21 inverted and the medicament plunger in an intermediate drawn position;

FIG. 23 is a perspective view of the medicament storage vial and reconstitution device of FIG. 22 disconnected from one another after all of the medicament is drawn into the syringe.

DETAILED DESCRIPTION OF THE EMBODIMENTS

Figure 1:
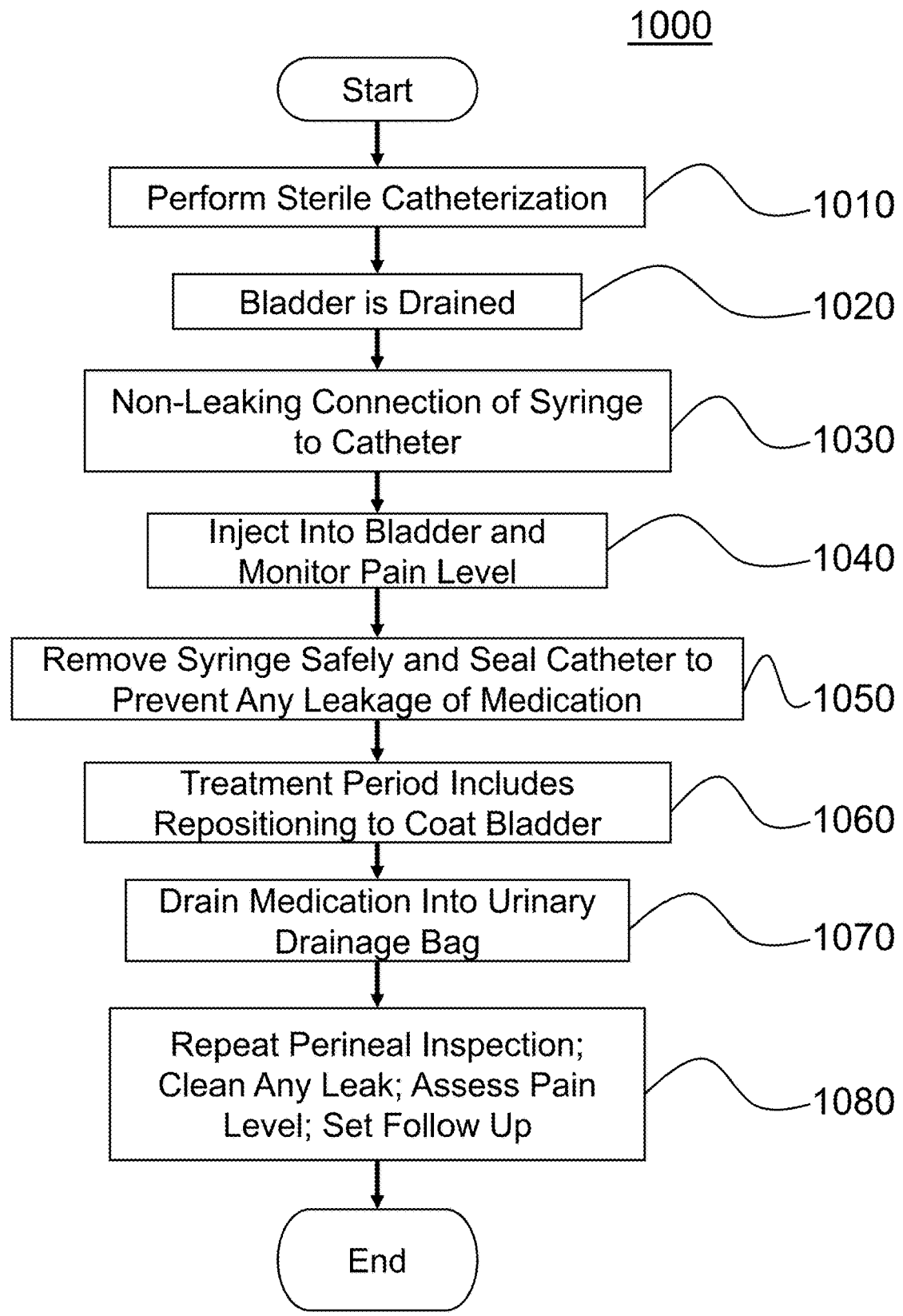
FIG. 1 is a process flow chart for carrying out an intravesical, bladder cancer treatment procedure according to the prior art.

As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one skilled in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the features of the systems, apparatuses, and methods that are regarded as novel, it is believed that the systems, apparatuses, and methods will be better understood from a consideration of the following description in conjunction with the drawing figures, in which like reference numerals are carried forward.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Alternate embodiments may be devised without departing from the spirit or the scope of the invention. Additionally, well-known elements of exemplary embodiments of the systems, apparatuses, and methods will not be described in detail or will be omitted so as not to obscure the relevant details of the systems, apparatuses, and methods.

Before the systems, apparatuses, and methods are disclosed and described, it is to be understood that the terminology used herein is for the purpose of describing particular embodiments only and is not intended to be limiting. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element. The terms "including" and/or "having," as used herein, are defined as comprising (i.e., open language). The terms "a" or "an", as used herein, are defined as one or more than one. The term "plurality," as used herein, is defined as two or more than two. The term "another," as used herein, is defined as at least a second or more. The description may use the terms "embodiment" or "embodiments," which may each refer to one or more of the same or different embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact (e.g., directly coupled). However, "coupled" may also mean that two or more elements are not in direct contact with each other, but yet still cooperate or interact with each other (e.g., indirectly coupled).

For the purposes of the description, a phrase in the form "A/B" or in the form "A and/or B" or in the form "at least one of A and B" means (A), (B), or (A and B), where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables, for example, a phrase in the form "at least one of A, B, and C" means (A), (B), (C), (A and B), (A and C), (B and C), or (A, B and C).

Relational terms such as first and second, top and bottom, and the like may be used solely to distinguish one entity or action from another entity or action without necessarily requiring or implying any actual such relationship or order between such entities or actions. The description may use perspective-based descriptions such as up/down, back/front, top/bottom, and proximal/distal. Such descriptions are merely used to facilitate the discussion and are not intended to restrict the application of disclosed embodiments. Various operations may be described as multiple discrete operations in turn, in a manner that may be helpful in understanding embodiments; however, the order of description should not be construed to imply that these operations are order dependent.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

Herein various embodiments of the systems, apparatuses, and methods are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Figure 2:
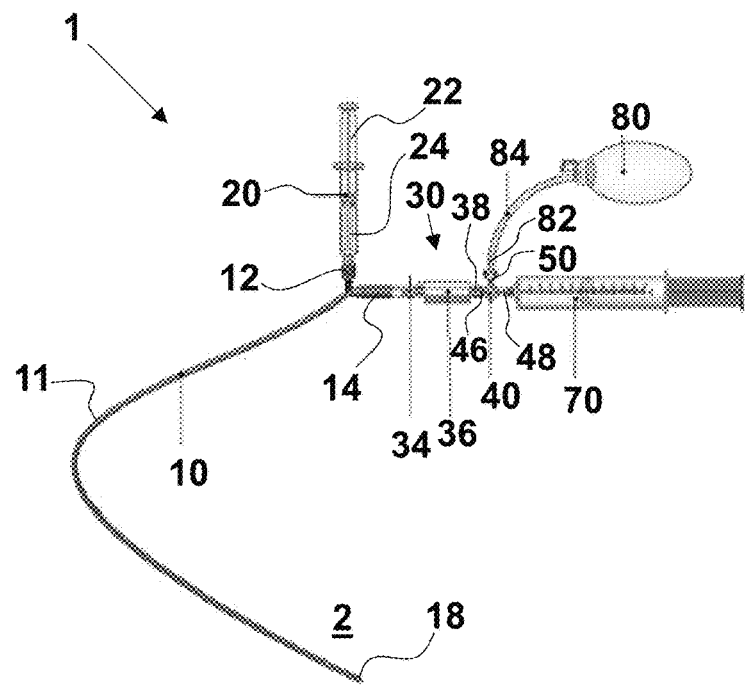
FIG. 2 is a fragmentary and perspective view of an exemplary embodiment of a closed-system, drug administering catheter for bladder chemotherapy treatment with a urinary catheter and a balloon inflation syringe in a ready-to-use state.
Figure 3:
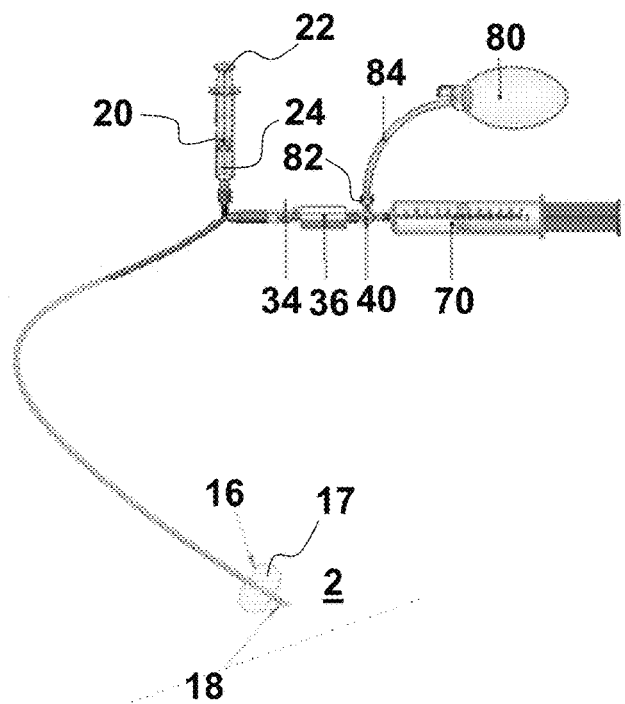
FIG. 3 is a fragmentary and perspective view of the catheter of FIG. 1 with the syringe in a depressed state and the balloon inflation catheter in a balloon-inflated state.
Figure 4:
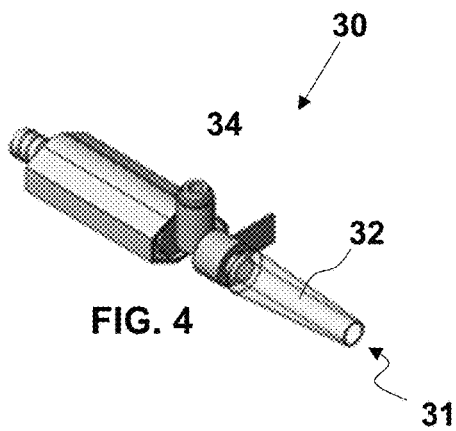
FIG. 4 is a perspective and partially transparent view of an exemplary embodiment of a unidirectional catheter adapter.
Figure 5:
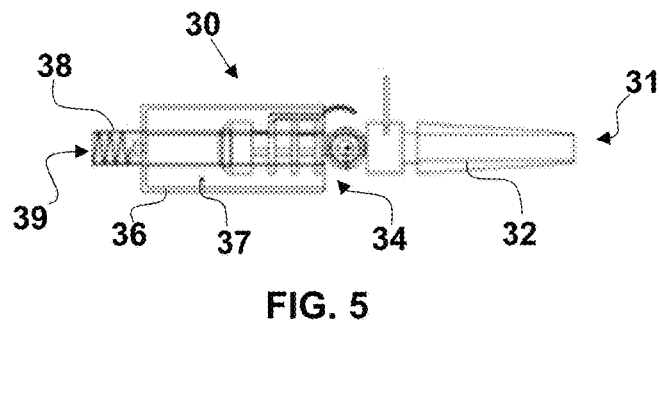
FIG. 5 is a top side elevational cross-sectional view of the catheter adapter of FIG. 4.
Figure 7:
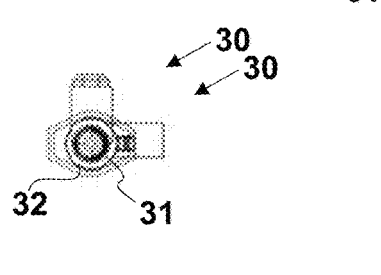
FIG. 7 is a side elevational cross-sectional view of the catheter adapter of FIG. 4.
Figure 6:
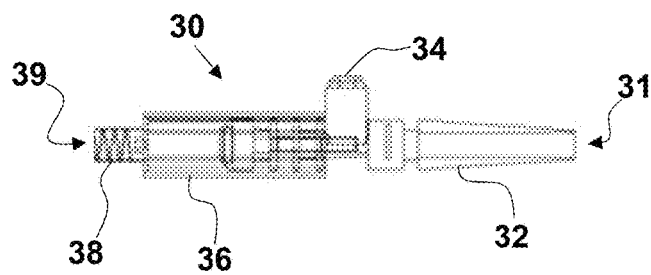
FIG. 6 is a cross-sectional plan view of the catheter adapter of FIG. 4 from the distal end.

Described now are exemplary embodiments. Referring now to the figures of the drawings in detail and first, particularly to FIG. 2, there is shown a first exemplary embodiment of a closed-system, drug-administering catheter system 1, e.g., for bladder chemotherapy treatment. A urethral catheter 10 comprising an inflation lumen, a main lumen, and a tip 18. An inflation port 12 is fluidically open at a proximal end of the inflation lumen and a medicament port 14 is fluidically open at a proximal end of the main lumen. The distal end of the inflation lumen exits into an inflatable balloon 16 defining therein an inflation chamber 17 surrounding material of the catheter 10 defining the drain lumen and a distal portion of the inflation lumen within at least a portion of the longitudinal extent of the balloon 16. A distal tip of an inflation syringe 20 is removably connected to the inflation port 12 of the inflation lumen (which is, e.g., through a luer connector). An exemplary embodiment of the syringe 20 is a 10 ml syringe, but the size can be any amount needed for the particular catheter 10. In use, a plunger 22 of the inflation syringe 20 rests slidably within a fluid chamber of the syringe 20 and the fluid chamber is filled with an inflation fluid 24, e.g., saline. The physician or other medical staff depresses the plunger 22 to move the inflation fluid 24 through the inflation lumen and into the inflation chamber 17 of the balloon 16. In FIG. 2, the syringe 20 is in an unactuated state:
  the interior of the syringe 20 is loaded with saline 24;
  the plunger 22 is in an unactuated position; and
  the balloon 16 is not inflated.
In FIG. 3, in contrast, the syringe 20 is in an actuated state:
  the plunger 22 has been actuated (here at least partially or completely) and the saline 24 has filled the inflation chamber 17 causing the balloon 16 to inflate.
The distal end of the main lumen opens into the surroundings of the tip 18 through at least one orifice disposed at the tip 18 (typically, two opposing orifices) and, therefore, the main lumen is considered fluidically open into any environment 2 that surrounds the tip 18. Thus, the proximal orifice of the medicament port 14 (which is, e.g., defined by a luer connector) is fluidically connected through the main lumen to the environment 2 outside and surrounding the tip 18 of the catheter 10.

A closed-system transfer device or adapter 30 is shown in FIGS. 4 to 7. This adapter 30 allows pressure to equalize on both sides thereof (proximal/distal) when a fluid (e.g., a hazardous fluid) is passing through the adapter 30 in either direction but does not allow any part of that fluid to be exposed to the environment. This adapter 30 equalizes pressure so that no fluid is forced out into the environment (thereby, preventing leaks), and the pressure equalization ensures flow in only the direction where the most pressure is being applied at that time. Therefore, when, for example, a syringe plunger 76, is pushing fluid through from the syringe 70 through the catheter 10 and into the bladder, flow occurs distally without leak of the fluid into the environment. And, in another example, when a vacuum is applied to the second connector 70 of the stopcock 40, for example, by the pressure reservoir 80, leak-free waste retrieval in the opposite flow direction (proximally) will occur, as the greatest pressure exists in the bladder as compared to the pressure reservoir 80. Thus, the adapter 30 creates a closed-system connection between the catheter 10 and a stopcock 40, described in further detail below. An exemplary embodiment of the closed-system transfer device is manufactured by Equashield, LLC, and is referred to as the Equashield® luer lock connector (see https://www.equasheild.com/wp-content/uploads/2019/03/Technical-Specifications-update.pdf). This connector is used typically to enact a closed-pressure equalization for fluid transfer that prevents the escape of vapors. While the Equashield® luer lock connector is not envisioned for uses that the instant systems and methods provide, it can be used as the adapter 30 in an exemplary embodiment. The closed-system transfer adapter 30 comprises a hollow distal connector 32 defining a distal orifice 31 that, when the adapter 30 is connected removably to the medicament port 14 of the catheter 10, defines a flow channel fluidically connecting the distal connector 32 to the main lumen. In the exemplary embodiment of the Equashield® luer lock connector 30, there is a hollow proximal connector 38 defining a proximal orifice that, when the adapter 30 is connected to the stopcock 40, creates a close-system connection between the medicament port 14 of the urethral catheter 10 and the various lumens of the stopcock 40 through the one lumen to which the adapter 30 is connected (the drain lumen of the catheter 10). In an exemplary embodiment, the proximal connector 38 is one of the male and female parts of a standard luer connector. Here, the proximal connector 38 is shown as the male part of the luer connector. The closed-system transfer adapter 30 has a body 36, in which is disposed a pressure-equalization valve 34. The body 36 defines a pressure equalization chamber 37.

Figure 8:
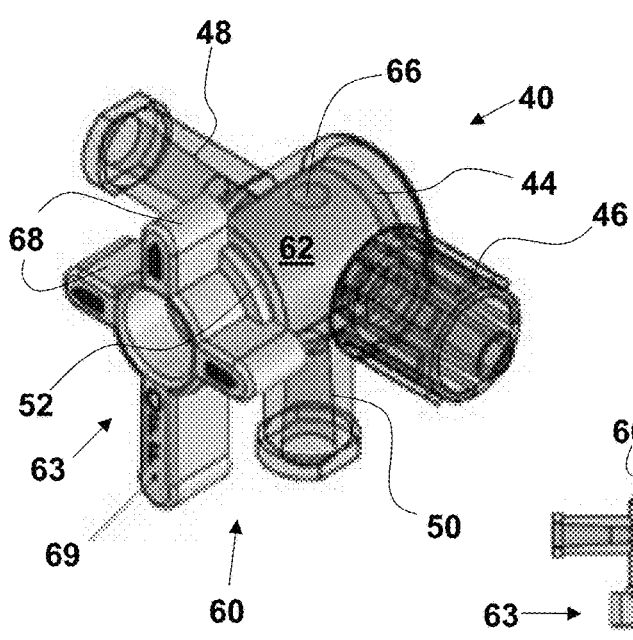
FIG. 8 is a perspective and partially transparent view of an exemplary embodiment of a stopcock in a lower-off position.

The stopcock 40 is illustrated in FIGS. 8 to 11. As can be seen in FIG. 8, the stopcock 40 is configured, in this exemplary embodiment, as a three-way stopcock valve, comprising a body 42 defining an interior plenum 44 fluidically connected to an internal lumen of a hollow first connector 46, an internal lumen of a hollow second connector 48, an internal lumen of a hollow third connector 50, and a diverter orifice 52. Rotatably attached to the body 42 in the diverter orifice 52 and fluid-tightly sealed therein is a diverter 60. In this manner, the diverter 60 can be rotated to fluidically connect/disconnect any number of the internal lumens of the first, second, and third connectors 46, 48, 50 to/from one another depending on the shape of internal lumens traversing within and positions of lumen end openings on a central body 62 of the diverter 60 that is disposed within the plenum 44 and fluidically communicating with the internal lumens of the first, second, and third connectors 46, 48, 50. In the exemplary embodiment shown in FIGS. 8 to 11, the first connector 46 is to be connected removably to the proximal connector 38 of the catheter adapter 30. Therefore, in the exemplary configuration shown, the first connector 46 is a female part of a luer connector. The second connector 48 is to be connected removably to a distal output 72 of a medicament injector 70, which will be described in further detail below. For a typical surgical syringe as the injector 70, the distal end opening of the surgical syringe is formed as a male part of a lure connector. Therefore, the second connector 48 can be a female part of a lure connector. Alternatively, as within the configuration shown, the second connector 46 is a barb adapter, e.g., a ⅛" barb adapter. Finally, the third connector 50 is to be connected removably to a reservoir connector 82 that leads to or is an input of a medicament pressure reservoir 80, which will be described in further detail below. As with the first and second connectors 46, 48, the third connector 50 can be any removable, fluid-tight medical connector. In the exemplary embodiment, the third connector 50 is a barb adapter, e.g., a ⅛" barb adapter.

Figures 11, 12:
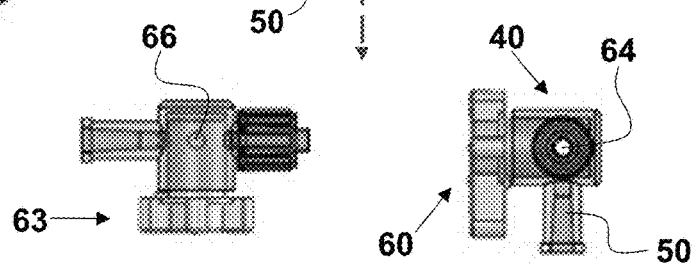
FIG. 11 is a top plan and partially transparent view of the stopcock of FIG. 8.
FIG. 12 is a right side elevational and partially transparent view of the stopcock of FIG. 8.

The central body 62 of the diverter 60 is formed with first and second internal lumens 64, 66 (see FIGS. 8 and 12, respectively). In the initial or introduction or administration position or state, which is shown in all of FIGS. 8, 9, 11, and 12, the first internal lumen 64 fluidically connects the internal lumens of the first and second connectors 46, 48 to one another. Thus, fluid (e.g., medicament 74) provided from the medicament injector 70 into the plenum 44 will enter through the second connector 48 and exit through the first connector 46. In this initial position, the central body 62 of the diverter 64 blocks and seals off the internal lumen of the third connector 50 from the plenum 44. As described in further detail below, this introduction state allows the user to inject medicament 74 through and out the distal opening of the main lumen of the catheter 10 into the environment 2 surrounding the tip 18 of the catheter 10, which in a bladder chemotherapy treatment is the space surrounded by the internal lining of the bladder.

Figure 9:
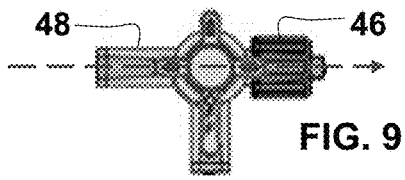
FIG. 9 is a front side elevational and partially transparent view of the stopcock of FIG. 8.
Figure 10:
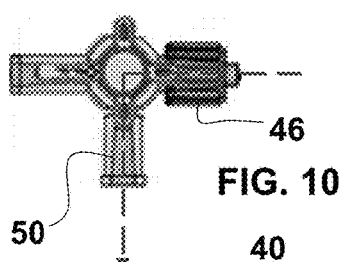
FIG. 10 is a front side elevational and partially transparent view of the stopcock of FIG. 8 in a left-off position.

The second internal lumen 66 is formed to fluidically connect the third connector 50 to the first connector 46 when the diverter 60 is rotated to the position shown in FIG. 9 into a final or drainage position or state that is ninety degrees (90°) clockwise from the introduction position (FIGS. 8, 9, 11, and 12). Thus, fluid within the catheter 10 and, in particular, within the environment 2 surrounding the tip 18 can be drawn out from the environment 2, through the catheter 10, through the third connector 50, and into the reservoir conduit 84 to, for example, ultimately be stored in the medicament pressure reservoir 80. In this drainage state, the central body 62 of the diverter 64 blocks and seals off the internal lumen of the second connector 48 from the plenum 44.

Described with respect to devices, systems, and methods above is the use of a single surgical syringe, which is not a limitation for the medicament injector 70. In another non-illustrated embodiment, the second connector 48 can be or can be attached to a Y-connector or any greater number of inputs so that 2 or 3 or more medicaments 74 can be provided through the catheter 10 in a given procedure. For example, if the surgeon wants to dilute the medicament 74 in a first injector 70, the Y-connector can be or be attached to the second connector and the first syringe with the medicament 74 attached to one input of the Y-connector and a second syringe (or other supply like a reservoir) filled with saline, for example, can be attached to the second input of the Y-connector. This can be expanded incrementally for 3, 4, or more inputs to connectors with a greater number of inputs. This scenario is typical as different surgeons and/or hospitals have different protocols or preferences in administration of such medicaments 74, and this also allows for simultaneous or serially injected fluids comprising what is referred to in the art as a chemotherapy cocktail. An exemplary embodiment of a stopcock 40' with an integral first W-connector 46' is shown in FIG. 18. In this embodiment, the three first connectors 46' can be attached to separate female luer connector parts and any number of which can be capped closed (temporarily or permanently) if not needed or needed later. The description of the stopcock 40 above is applicable to the stopcock 40' of FIG. 18 and, therefore, the text is not repeated here but is incorporated by reference in its entirety.

The words "initial" and "final" are used herein to describe two separate orientations and/or states and do not necessarily require or prescribe an order in which these positions are used. In an exemplary embodiment of a method for delivering and removing medicament described in further detail below, the initial position does come first in an exemplary process and the final position is entered after the initial position in that process. Other processes are envisioned to order these positions differently and to add one or more further internal lumens to the central body 62 as well as further connectors fluidically connected to the plenum 44 of the body 42 where the stopcock 40 is more than a three-way valve or one of the connections is a dual, a triple, or even more input/output orifices.

To rotate the diverter between the various positions of the stopcock 40, a portion of the body 62 of the diverter 60 extends out externally from the body 42 of the stopcock 40. Further, this external body portion or handle 63 is provided with grips 68, e.g., in the form of fins, that are shaped to permit a user to easily turn the diverter 60 between positions. In the exemplary embodiment shown, there are four fins 68 for gripping the handle 63 to thereby rotate the diverter 60 as desired. As can be seen from the various positions of the diverter 64 in the initial and final states (respectively, FIGS. 9 and 10), a single fin of the four fins 68 is positioned towards/above the respective closed-off connector in each of these state. Therefore, it is desirable to place an appropriate indicia on this portion of the handle 63 of the diverter 60 so that the user can easily see in which state the stopcock 40 rests; said another way, the indicia informs the user which lumen is closed off to prevent fluid flow therethrough and which lumens are open to permit fluid flow therethrough. In the exemplary embodiment of FIGS. 8 to 12, indicia in the form of the word "OFF" is placed on one fin 68 to create an off indicator 69.

As mentioned above, the third connector 50 of the stopcock 40 is connected removably to the reservoir connector 82, which leads to or is an input of a medicament pressure reservoir 80. The reservoir connector 82 can be any structure that fluid-tightly connects the third connector 50 to any conduit leading to or being the input of the pressure reservoir 80. In an exemplary embodiment shown in FIGS. 2 and 3 and, in particular, in the larger view of FIG. 13, the reservoir connector 82 is a male luer to ⅛" barb adapter and the conduit is a reservoir tube 84. The distal end of the reservoir tube 84 is fluid-tightly connected to the output of the reservoir connector 82 in a manner that substantially prevents any leaks of the medicament 74 that, ultimately, is to reside in the pressure reservoir 80 after a treatment procedure. An exemplary embodiment of the reservoir tube 84 is silicone tubing ⅛"×¼". The conduit and the connector can be integral and shorter or longer depending on a desired placement of the pressure reservoir 80.

To assemble the reservoir sub-assembly, the distal end of the reservoir connector 82 is fluid-tightly connected to the third connector 50. This can be, for example, merely a press-fit, or the connection can include one or more fasteners, such as an exterior clip and/or an adhesive. The distal end of the reservoir tube 84 is fluid-tightly connected to the proximal end of the reservoir connector 82. Here, in FIG. 13, the distal end of the silicone tube 84 is passed over the barb of the reservoir connector 82 and secured, for example, by a pressure fit and/or adhesive (in either a temporary manner or a permanent one). The proximal end of the reservoir tube 84 is fluid-tightly connected to the reservoir input 86, which, in the exemplary embodiment shown, is also a barb fitting. Accordingly, the proximal end of the silicone tube 84 is passed over the barb input 86 of the pressure reservoir 80 and secured, for example, by a pressure fit and/or adhesive (temporary or permanent).

The pressure reservoir 80 is any structure that can withstand and hold a level of negative pressure for a given amount of time that is at least as long as the desired treatment procedure (which is typically up to a few hours). One exemplary embodiment of the structure is one that can withstand between approximately −10 mmHg and approximately −250 mmHg, further, between approximately −100 mmHg and approximately −200, mmHg, in particular, approximately −167.4 mmHg. An exemplary embodiment of the structure is one that can be stored without negative pressure but then caused to withstand a negative pressure during or at the end of the procedure. The structure of the pressure reservoir 80 is able to store the medicament 74 after completing the treatment procedure and before ultimate disposal of the used medicament 74, whether disposal occurs along with or separate from the pressure reservoir 80. It is desirable, however, to dispose of all parts that contact the medicament 74 and, therefore, in an exemplary embodiment, the disposal occurs with all parts 10, 20, 30, 40, 70, and 80 of the system. An exemplary embodiment of the pressure reservoir 80 is a 100 cc surgical drain bulb. The surgical drain bulb has exterior bulb material defining an interior 81. Fluidically connecting the interior 81 to the environment outside the bulb (when disconnected from the reservoir tube 84) are two throughputs. The first is a reservoir input 86 for receiving the used medicament 74. This input is open to allow free flow of the used medicament 74 into the interior 81 of the pressure reservoir 80. The second throughput is a one-way pressure valve 88, which allows fluid (e.g., air) to exit the interior 81 of the pressure reservoir 80 but to not allow any fluid to enter the interior 81. This means that, if the reservoir input 86 is closed off, squeezing the bulb of the pressure reservoir 80 will cause the air in the interior 81 to exit through the one-way pressure valve 88 without allowing any fluid (e.g., air) back into the interior 81. Thus, until the reservoir input 86 is allowed to open, the bulb of the pressure reservoir 80 will remain in a squeezed-in or deflated or negatively pressurized state.

The pressure reservoir 80 can arrive at the user in various ways. In a first exemplary embodiment, the pressure reservoir 80 is already at negative pressure or the user causes the pressure reservoir 80 to exhibit negative pressure at any user-desired time. In the first, negative-pressure-delivered state, prior to assembly, the interior of the pressure reservoir 80 is reduced to exhibit a negative pressure and is sealed in that way until use during a procedure. In another exemplary embodiment of a surgical drain bulb that is not stored with negative pressure, the bulb 80 is compressed by the physician or medical staff who conduct the procedure to remove air (or another gas or gas mixture) from the bulb 80 through the one-way pressure valve 88. In this state, the structure of the bulb 80 having potential energy stored in the collapsed state occurs during the procedure and can be released when desired to expand the bulb 80 and, thereby, draw any fluid that is fluidically connected to the reservoir connector 82 into the interior of the pressure reservoir 80. Thus, when the stopcock 40 is rotated to allow flow of fluid in the catheter 10, or in the environment 2 of the tip 18 through the catheter 10, into the stopcock 40, the release of the stored energy in the pressure reservoir 80 will cause the bulb to expand and draw liquid present in the bladder, including the used medicament 74, into the interior 81 of the bulb 80 for storage and/or disposal. Each state in the U.S. has its own rules for medical waste disposal and, in particular, for chemotherapy waste disposal. The American Society of Health System Pharmacists (ASHP) and the National Institute for Occupational Safety and Health (NIOSH) also promulgate guidelines on handling and disposal of hazardous drugs. Because there are various standards and the standards change depending upon where a procedure is carried out, as used herein, the terms disposable, proper disposal, safe disposal, secure disposal, ultimate disposal, or the like of medicament or of the system or its components means placing the material in a discarding state that complies with local guidelines or standards.

Another exemplary embodiment of the pressure reservoir 80 is in the shape of a standard Foley catheter bag but that is made from a material that does not erode from chemotherapy medicaments. It is noted that PVC erodes from such medicaments but that, for example, di(2-ethylhexyl) phthalate (DEHP), dioctyl phthalate (DOP), and bis(2-ethylhexyl) phthalate (BEHP) do not erode and, therefore, the Foley catheter bag can be made of one or more of these chemicals.

The final part of the system 1 is the medicament injector 70, which, in the exemplary embodiment, is a medicament syringe comprising a medicament body 71 defining an internal medicament chamber 78 and a medicament plunger 76 slidably connected within the medicament chamber 78. As set forth above, the second connector 48 is to be connected removably to the distal medicament output 72 of the medicament injector 70. Thus, in the exemplary form of a surgical syringe, the distal medicament output 82 is an end opening of the medicament body 71 formed as a male part of a lure connector. With the second connector 48 formed as a female part of the lure connector, the two parts can be removably, fluid-tightly connected to one another in a closed-system. The medicament injector 70 can be filled with the medicament 74 prior to being assembled to the system 1 and sealed to prevent any medicament 74 from spilling out before connected to the second connector 48. Alternatively, the medicament injector 70 can be filled with the medicament 74 during assembly and either permanently or removably connected to the second connector 48 at the manufacturer. Thus, in the latter case, the system 1 arrives at the physician with the medicament injector 80 as an integral part for use during a procedure. Other exemplary configurations of the medicament injector 70 include an elastomeric pump.

Embodiments of the medicament hereinabove start with the medicament as a liquid. Some of the chemotherapy drugs envisioned for use with the systems, devices, and methods described herein require chilling to preserve longevity of the medicament. Not only is the chilling requirement expensive, for a closed-system it might require that all of the system be placed in chilled storage before use instead of just the medicament injector. This is not efficient both in terms of cost and storage space, especially where chilled storage space is has both a high cost and is limited in terms of volume. Accordingly, in an exemplary embodiment, the medicament 74 can start as a powder or other form of solid within the medicament injector 70. The process for preparing the medicament 74 for use with the system 10 starts with reconstituting the drug as shown in the progression in FIGS. 19 to 23. To begin, the medicament 74 to be reconstituted is placed, for example, in a standard medical grade vial 100 (e.g., glass) containing the solid (e.g., powder) drug product (which has a minimum capacity of approximately 60 mL to approximately 80 mL) at the manufacturer and is stored in this way until use is desired. A reconstitution system 90, such as the Closed System Drug Transfer Device manufactured by Equashield® (see https://www.equashield.com/wp-content/uploads/2019/03/Technical-Specifications-update.pdf and which is incorporated herein in its entirety), is provided. The exemplary reconstitution system 90 includes a flush syringe unit 92 (e.g., approximately 60 mL) having closed-system adaptor (Equashield® Ref #SU-60/2) and a closed system vial spike adapter 94 (Equashield® Ref #VA-20/2) or another adapter size to match the size of the vial 100. Another exemplary reconstitution system is the EmGyn Kit™ (Emergency Gynecologic Methotrexate Kit) that is produced by EDGEpharma®. The medicament injector 70 is filled with the reconstitution liquid 102 (e.g., saline) and is removably attached to the flush syringe unit 92; the injector 70 is caused to inject the reconstitution liquid 102 into the vial 100 to create the medicament 74, as shown in the progression from FIG. 19 to FIG. 21. Then, the entire assembly 70, 92, 94, 100 is inverted, as shown in FIG. 22, and the medicament syringe plunger 76 is moved away from the vial 100 to draw the medicament 74 into the medicament chamber 78. The plunger 76 is only moved distally to inject air into the vial 100. When all of the medicament 74 is in the medicament chamber 78, as shown in FIG. 23, the vial 100 and the adaptor 94 and the syringe unit 92 are removed from the medicament injector 70 and the medicament injector is attached to the stopcock 40, which can be a single, double, or triple port entry as shown and described or, e.g., the EmGyn Kit™, which hydrates a powder to prepare the medicament.

In another alternative embodiment of the reconstitution system, a more advanced mixing technique incorporates the known coffee-dispensing configuration where a pressurized bag or capsule is divided by a non-permeable membrane to separate the reconstitution liquid 102 (e.g., a saline solution) from the solid (e.g., powder) medicament 74. When it is time to use the system 10 with the medicament 74, a mechanism inside the capsule breaks the membrane to allow mixing of the two and, thereby, reconstitute the medicament 74. The bag/capsule can be shaken, massaged, or agitated to mix the medicament 74 sufficiently for use. Pressure of the bag/capsule can then be released by unclamping the connective device (e.g., tubing) fluidically leading to the second connector 48 of the stopcock 40. The internal pressure causes the reconstituted medicament 74 to be pushed through the stopcock 40, the catheter adapter 30, and the catheter 10 and into the environment 2, e.g., the bladder. Alternatively, the capsule/bag can be unpressurized and attached to a medicament injector 70 that can squeeze or otherwise press the medicament 74 through the system 10 after the medicament 74 is fully reconstituted. It is noted that the bag/capsule is of a material that is resistant or impervious to chemotherapy drug interactions.

Figure 24:
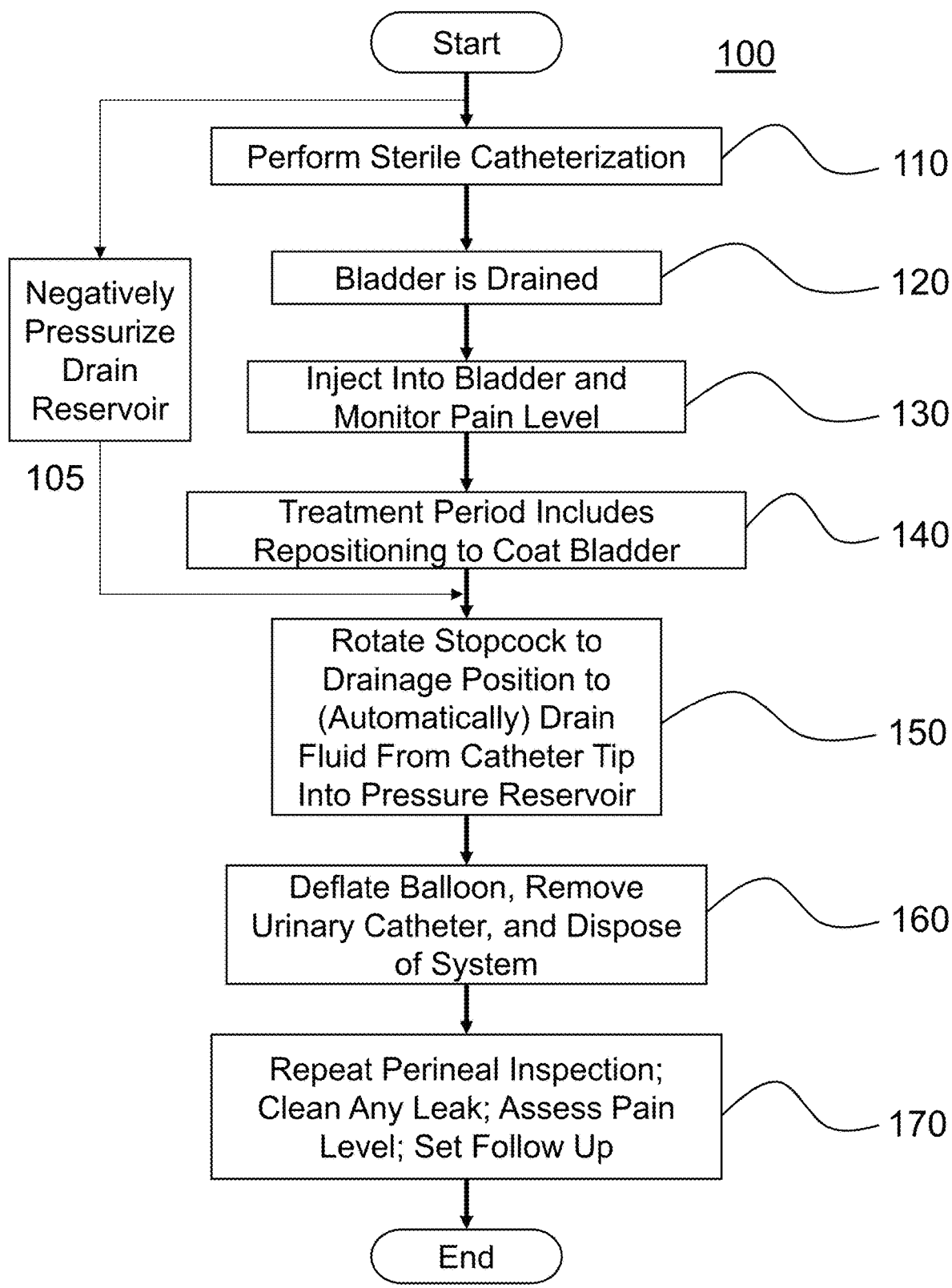
FIG. 24 is a process flow chart for carrying out an intravesical, bladder cancer treatment procedure with the system of FIG. 1.

An exemplary procedure 100 for intravesical chemotherapy therapy of bladder cancer using the system 1 is described with respect to FIG. 24. Prior to treatment, a physical examination takes place, including patient identification, confirmation of physician order to treat, assessment of vital signs and general well-being, assessment of ability to retain fluid in the bladder for necessary treatment time, urine analysis, and the perineal inspection including pain assessment (bladder, back, and pelvic). Once the patient is cleared from this examination, they are asked to void their bladder (the bladder can also be drained through a Foley catheter if the patient is unable to do so). The procedure 100 can then begin. Sterile catheterization is performed with the catheter 10 in step 110, including inflation of the balloon 16. The bladder is drained in step 120. The entire system 1 shown in FIG. 2 is already connected together (which is referred to herein as an assembly), thus, there is no need to perform a connection step as in the prior art, which step could result in exposure to the medicament. The stopcock 40 of the system 1 is already pre-set to the introduction position (see, e.g., FIGS. 8 and 10). Thus, in step 130, the medicament 74 is slowly injected while assessing the patient's pain level. The system 1 can be left alone during the treatment period in step 140. The medicament 74 is held in the bladder for the specified treatment time (usually one to two hours) During this treatment period, the patient could be asked to roll, from left to right, and to reposition every fifteen minutes or so to ensure that the drug coats the entire inner lining of the bladder. To even further ensure that the plunger 76 of the medicament injector 70 does not move, the medicament injector 70 can be provided with a lock, which holds the plunger 76 still until further movement is desired. Alternatively, the lock can be a one-way or permanent one, which locks the body 71 and the plunger 76 with respect to one another, thereby preventing any retraction of the medicament back into the injector 70. Exemplary forms of the lock include mechanisms such as press-fit, ratchet, cam, link, latch, cylinder, spring bolt, mortise, deadbolt. Another addition or alternative, is that the stopcock 40 can be rotated to an intermediate position where none of the first, second, or third connectors 46, 48, 50 are fluidically connected to one another. In this way, any fluid present in the catheter 10 or the bladder remains there until the stopcock 40 is rotated to one of the flow positions.

After the desired dwell time, in step 150, the stopcock 40 is rotated to the drainage position. At any time prior to step 150, the medicament pressure reservoir 80 is placed under negative pressure, as shown in step 105. Therefore, when the stopcock 40 is placed in the drainage position, substantially all or all of the fluid in the bladder is withdrawn, first through the catheter 10, then through the one-way valve of the unidirectional catheter adapter, then through the stopcock 40, then through the reservoir tube 84 (if any), and into the reservoir 80. In step 160, the balloon 16 of the catheter 10 is deflated and the catheter 10 is removed from the patient. The entire system 1 is disposed of in the acceptable or required manner. For example, the entire Genius system 1 (and any contaminated materials) can be place in a chemotherapy bag for safe disposal in a hazardous waste container or other secure disposal. Finally, in step 170, a perineal inspection is repeated, leaks are cleansed, the patient is assessed for pain again, and a follow-up appointment is scheduled.

As indicated above, the prior art procedure 1000 must take place in a hospital setting because the systems used could experience leakage of the dangerous medicament 74. However, with the system 1, all of the required controls are present to prevent any leakage. Thus, PPE is not mandatory (but still can be used) because there is no transfer of the medicament. This means that, with the system 1, urologists can now perform the procedure themselves in their outpatient clinics.

It is understood that no system transferring hazardous medicament 74 is perfectly closed and there is the possibility of a minimal amount of leakage during a given procedure. Thus, as used herein, "leak/s" or "leak-free" or "without leakage" or "preventing leakage" or "prevent any leakage" or similar language with respect to the medicament 74, means that the medicament 74 substantially does not enter the environment of the patient or of the medical staff in a quantity that those of skill in the art deem to be minimal or safe dependent upon the particular medicament 74 being used.

There are a few significant benefits that the above-described systems, devices, and methods provide with respect to profitability. This lies in the ability for the system to be reimbursed under two separate standardized insurance processes. The first process relates to the medical provider of the system. The system, used with or without a medicament, allows a provider to bill the product under a commercial medical plan or Medicare (Part B) using a J code submission. As is known, the J Code is a Healthcare Common Procedure Coding System (HCPCS) Level II alphanumeric code issued by the Centers for Medicare and Medicaid Services (CMS) to identify and describe a drug product, which allows a provider to submit a bill for a procedure. J codes are a subset of the HCPCS Level II code set used to primarily identify injectable drugs. HCPCS J codes typically include drugs that cannot be self-administered, are reasonable and necessary for the treatment of the injury or illness, and are considered effective by the FDA, among other requirements. In addition, they must meet all the general requirements for coverage of items as incident to a physician's/surgeon's services. These are often referred to in the healthcare benefits business as "J code" drugs. HCPCS Level I codes are the Current Procedural Terminology (CPT®) code set that accompanies a "J code" and are used by medical practitioners to bill for claims on medical procedures with a patient's healthcare insurance.

The second process relates to the pharmacy provider who dispenses the system. Drug establishments are required to provide FDA with a current list of all drugs manufactured, prepared, propagated, compounded, or processed for sale in the U.S. at their facilities. Drugs are identified and reported using a unique, three-segment number called the National Drug Code (NDC), which serves as the FDA's identifier for drugs. FDA publishes the listed NDC numbers in the NDC Directory, which is updated daily. The NDC Directory contains information on active and certified finished and unfinished drugs submitted to FDA in structured product labeling (SPL) electronic listing files by labelers. A labeler may be a manufacturer, including repackage or relabeled, or the entity named on the product label. By using the device with medicament, this allows a pharmacy to bill the Pharmacy Benefit Manager (PBM) commercial or Part D insurance for a drug component having an NDC, in addition to the drug component accompanied with the device where the device would be needed to administer the medicament. The device would be considered an additional "Per Diem" charge which would be reflected in the Average wholesale price (AWP).

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The foregoing description and accompanying drawings illustrate the principles, exemplary embodiments, and modes of operation of the systems, apparatuses, and methods. However, the systems, apparatuses, and methods should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the systems, apparatuses, and methods as defined by the following claims.

What is claimed is:

1. A closed-system, drug administering catheter assembly, comprising:
   a transfer adapter, a stopcock, a medicament injector containing chemotherapy medicament, a medicament pressure reservoir, and a urethral balloon catheter comprising a drain lumen and a distal tip, all connected together in a closed-system;
   the medicament injector being configured to inject the chemotherapy medicament through the stopcock, the drain lumen, and into an environment of the distal tip within a patient's organ without leakage of the chemotherapy medicament from the patient into an environment of the patient; and
   the medicament pressure reservoir being configured to store negative pressure that withdraws from the organ used chemotherapy medicament through the drain lumen and the stopcock and holds the used chemotherapy medicament in the medicament pressure reservoir without leakage of the used chemotherapy medicament into the environment of the patient.

2. The assembly according to claim 1, wherein the organ is a human bladder.

3. The assembly according to claim 1, wherein the transfer adapter comprises:
   a distal connector comprising a distal orifice;
   a proximal connector comprising a proximal orifice; and
   an intermediate pressure-equalization valve fluidically connecting the distal orifice to the proximal orifice and configured to equalize pressure across the transfer adapter without leakage of liquid therein.

4. The assembly according to claim 1, wherein the stopcock comprises:
   an introductory flow state that permits fluidic flow between the medicament injector and the organ through the drain lumen;
   a closed state that substantially prevents liquid from travelling through the stopcock; and
   a drainage flow state that permits fluidic flow between the organ and the pressure reservoir through the drain lumen.

5. The assembly according to claim 1, wherein the stopcock is a three-way stopcock valve.

6. The assembly according to claim 1, wherein the stopcock comprises:
   a hollow first connector comprising a first internal lumen;
   a hollow second connector comprising a second internal lumen;
   a hollow third connector comprising a third internal lumen;
   a body defining an interior plenum fluidically connected to the first, second, and third internal lumens and a diverter orifice; and
   a diverter rotatably attached to the body in the diverter orifice and fluid-tightly sealed therein, the diverter configured to rotate and, thereby, fluidically connect or disconnect any number of the first, second, and third internal lumens.

7. The assembly according to claim 6, wherein:
   the first connector is connected to the transfer adapter;
   the second connector is connected to the medicament injector; and
   the third connector is connected to the pressure reservoir.

8. The assembly according to claim 7, wherein the diverter comprises:
   an administration state in which the internal lumens of the first and second connectors are fluidically connected to one another to permit medicament from the medicament injector to enter the second connector and exit through the first connector; and
   a drainage state in which the internal lumens of the first and third connector are fluidically connected to one another to permit fluid within the catheter drain lumen and the environment surrounding the distal tip to be drawn out from the environment, through the catheter, through the third connector, and into the pressure reservoir.

9. The assembly according to claim 6, wherein the diverter comprises a handle shaped to permit a user to turn the diverter between positions within the body and, thereby, fluidically connect or disconnect any number of the first, second, and third internal lumens.

10. The assembly according to claim 1, wherein the medicament injector has a lock that prevents fluid flow through independent of a position of the stopcock.

11. The assembly according to claim 1, wherein the chemotherapy medicament is hazardous liquid chemotherapy medicament.

12. The assembly according to claim 11, wherein the chemotherapy medicament is at least one of mitomycin and gemcitabine.

13. The assembly according to claim 1, wherein the chemotherapy medicament:
   is first stored in a solid form; and
   is then reconstituted in the medicament injector.

14. The assembly according to claim 1, wherein the pressure reservoir is of a fortified material substantially impervious to the chemotherapy medicament.

15. The assembly according to claim 14, wherein the material is at least one of di(2-ethylhexyl) phthalate (DEHP), dioctyl phthalate (DOP), and bis(2-ethylhexyl) phthalate (BEHP).

16. The assembly according to claim 1, wherein the pressure reservoir is a surgical drain bulb.

17. The assembly according to claim 16, wherein the negative pressure is created by a compression of the drain bulb.

18. The assembly according to claim 1, wherein the pressure reservoir is configured:
   to hold a level of negative pressure for a given amount of time at least as long as a chemotherapy treatment procedure; and to store the chemotherapy medicament after completing the chemotherapy treatment procedure and at least up until ultimate disposal of the used chemotherapy medicament.

19. The assembly according to claim 1, wherein:
the balloon catheter comprises a proximal medicament port fluidically connected to the drain lumen;
the transfer adapter comprises:
a distal connector comprising a distal orifice;
a proximal connector comprising a proximal orifice; and
an intermediate pressure-equalization valve fluidically connecting the distal orifice to the proximal orifice and configured to equalize pressure across the transfer adapter;
the stopcock comprises:
a body defining a plenum;
a first connector fluidically connected to the proximal connector of the transfer adapter;
a second connector;
a third connector; and
a central body disposed in the plenum and configured to selectively connect at least one of the second and third connectors to the first connector;
the medicament injector:
is filled with the chemotherapy medicament;
comprises a distal medicament output fluidically connected to the second connector; and
is configured to inject the medicament through the stopcock, the drain lumen and into an environment of the distal tip;
the medicament pressure reservoir comprises:
a reservoir input fluidically connected to the third connector; and
a body:
defining an interior fluidically connected to the reservoir input; and
configured to exert a negative pressure upon the third connector such that, responsive to fluidically connecting the drain lumen to the third connector through the stopcock, the negative pressure in the interior draws fluid in the environment of the distal tip through the drain lumen, through the transfer adapter, and into the interior of the pressure reservoir; and
the catheter, the transfer adapter, the stopcock, the medicament injector, and the pressure reservoir together comprise a disposable closed-system responsive to being connected together with the medicament in the medicament injector.

20. The assembly according to claim 1, wherein the closed-system of the transfer adapter, the stopcock, the medicament injector, the chemotherapy medicament, the medicament pressure reservoir, and the urethral balloon catheter is disposable.

21. The assembly according to claim 1, wherein the closed-system of the transfer adapter, the stopcock, the medicament injector, the chemotherapy medicament, the medicament pressure reservoir, and the urethral balloon catheter is billable:
by a provider under a medical insurance plan; and
by a pharmacy provider dispensing the closed-system product for a drug component in addition to the medicament accompanying the closed-system product.

22. The assembly according to claim 21, wherein the closed-system product is:
first a registered medical device; and
then is a registered combination medical device with drug to be processed by manufacturers and pharmaceutical suppliers.

23. A closed-system, drug administering catheter assembly, comprising:
a urethral balloon catheter comprising a drain lumen and a distal tip;
a transfer adapter fluidically connected to the drain lumen;
a stopcock fluidically connected to the transfer adapter;
a medicament injector fluidically connected to the stopcock;
a medicament pressure reservoir fluidically connected to the stopcock; and
the transfer adapter, the stopcock, the medicament injector, the medicament pressure reservoir, and the balloon catheter connected together in a closed-system such that hazardous liquid chemotherapy medicament in the medicament injector is configured to be:
injected through the stopcock, the drain lumen, and into an environment of the distal tip within a patient's human bladder;
left in the bladder for a given amount of time; and
then withdrawn from the bladder through the drain lumen and the stopcock and into the medicament pressure reservoir by negative pressure stored in the medicament pressure reservoir, without leakage of the chemotherapy medicament from the patient into an environment of the patient.

24. The assembly according to claim 23, wherein the transfer adapter comprises:
a distal connector comprising a distal orifice;
a proximal connector comprising a proximal orifice; and
an intermediate pressure-equalization valve fluidically connecting the distal orifice to the proximal orifice and configured to equalize pressure across the transfer adapter without leakage of liquid therein.

25. The assembly according to claim 23, wherein the stopcock comprises:
an introductory flow state that permits fluidic flow between the medicament injector and the bladder through the drain lumen;
a closed state that substantially prevents liquid from travelling through the stopcock; and
a drainage flow state that permits fluidic flow between the bladder and the pressure reservoir through the drain lumen.

26. The assembly according to claim 23, wherein the stopcock is a three-way stopcock valve.

27. The assembly according to claim 23, wherein the stopcock comprises:
a hollow first connector comprising a first internal lumen;
a hollow second connector comprising a second internal lumen;
a hollow third connector comprising a third internal lumen;
a body defining an interior plenum fluidically connected to the first, second, and third internal lumens and a diverter orifice; and
a diverter rotatably attached to the body in the diverter orifice and fluid-tightly sealed therein, the diverter configured to rotate and, thereby, fluidically connect or disconnect any number of the first, second, and third internal lumens.

28. The assembly according to claim 27, wherein:
the first connector is connected to the transfer adapter;
the second connector is connected to the medicament injector; and
the third connector is connected to the pressure reservoir.

29. The assembly according to claim 28, wherein the diverter comprises:
an administration state in which the internal lumens of the first and second connectors are fluidically connected to one another to permit medicament from the medicament injector to enter the second connector and exit through the first connector; and
a drainage state in which the internal lumens of the first and third connector are fluidically connected to one another to permit fluid within the catheter drain lumen and the environment surrounding the distal tip to be drawn out front the environment, through the catheter, through the third connector, and into the pressure reservoir.

30. The assembly according to claim 27, wherein the diverter comprises a handle shaped to permit a user to turn the diverter between positions within the body and, thereby, fluidically connect or disconnect any number of the first, second, and third internal lumens.

31. The assembly according to claim 23, wherein the medicament injector has a lock that prevents fluid flow through independent of a position of the stopcock.

32. The assembly according to claim 23, wherein the chemotherapy medicament is hazardous liquid chemotherapy medicament.

33. The assembly according to claim 32, wherein the chemotherapy medicament is at least one of mitomycin and gemcitabine.

34. The assembly according to claim 23, wherein the chemotherapy medicament:
is first stored in a solid form; and
is then reconstituted in the medicament injector.

35. The assembly according to claim 23, wherein the pressure reservoir is of a fortified material substantially impervious to the chemotherapy medicament.

36. The assembly according to claim 35, wherein the material is at least one of di(2-ethylhexyl) phthalate (DEHP), dioctyl phthalate (DOP), and bis(2-ethylhexyl) phthalate (BEHP).

37. The assembly according to claim 23, wherein the pressure reservoir is a surgical drain bulb.

38. The assembly according to claim 37, wherein the negative pressure is created by a compression of the drain bulb.

39. The assembly according to claim 23, wherein the pressure reservoir is configured:
to hold a level of negative pressure for a given amount of time at least as long as a chemotherapy treatment procedure; and
to store the chemotherapy medicament after completing the chemotherapy treatment procedure and at least up until ultimate disposal of the used chemotherapy medicament.

40. The assembly according to claim 23, wherein:
the balloon catheter comprises a proximal medicament port fluidically connected to the drain lumen;
the transfer adapter comprises:
a distal connector comprising a distal orifice;
a proximal connector comprising a proximal orifice; and
an intermediate pressure-equalization valve fluidically connecting the distal orifice to the proximal orifice and configured to equalize pressure across the transfer adapter; the stopcock comprises:
a body defining a plenum;
a first connector fluidically connected to the proximal connector of the transfer adapter;
a second connector;
a third connector; and
a central body disposed in the plenum and configured to selectively connect at least one of the second and third connectors to the first connector; the medicament injector:
is filled with the chemotherapy medicament;
comprises a distal medicament output fluidically connected to the second connector; and
is configured to inject the medicament through the stopcock, the drain lumen and into an environment of the distal tip;
the medicament pressure reservoir comprises:
a reservoir input fluidically connected to the third connector; and
a body:
defining an interior fluidically connected to the reservoir input; and
configured to exert a negative pressure upon the third connector such that, responsive to fluidically connecting the drain lumen to the third connector through the stopcock, the negative pressure in the interior draws fluid in the environment of the distal tip through the drain lumen, through the transfer adapter, and into the interior of the pressure reservoir; and
the catheter, the transfer adapter, the stopcock, the medicament injector, and the pressure reservoir together comprise a disposable closed-system responsive to being connected together with the medicament in the medicament injector.

41. The assembly according to claim 23, wherein the closed-system of the transfer adapter, the stopcock, the medicament injector, the chemotherapy medicament, the medicament pressure reservoir, and the urethral balloon catheter is disposable.

42. The assembly according to claim 23, wherein the closed-system of the transfer adapter, the stopcock, the medicament injector, the chemotherapy medicament, the medicament pressure reservoir, and the urethral balloon catheter is billable:
by a provider under a medical insurance plan; and
by a pharmacy provider dispensing the closed-system product for a drug component in addition to the medicament accompanying the closed-system product.

43. The assembly according to claim 42, wherein the closed-system product is:
first a registered medical device; and
then is a registered combination medical device with drug to be processed by manufacturers and pharmaceutical suppliers.

* * * * *

UNITED STATES PATENT AND TRADEMARK OFFICE
CERTIFICATE OF CORRECTION

PATENT NO. : 11,266,815 B1
APPLICATION NO. : 17/324780
DATED : March 8, 2022
INVENTOR(S) : Milena Bonanno and Charles Bonanno It is certified that error appears in the above-identified patent and that said Letters Patent is hereby corrected as shown below:

In the Specification

In Column 2, Line 5, replace "mitomycin" with "Mitomycin".
In Column 2, Line 6, replace "gemcitabine" with "Gemcitabine".
In Column 2, Line 16, insert an --a-- before "catheter".
In Column 2, Line 21, insert an --a-- before "catheter".
In Column 3, Line 31, replace "chemo- and immune-therapies" with "chemotherapies and immunotherapies".
In Column 6, Line 9, replace "comprises" with "comprising".
In Column 6, Line 26, replace "comprises" with "comprising".
In Column 6, Lines 44 and 45, delete "In accordance with another feature ,".
In Column 7, Line 1, after "defining" insert --a diverter orifice and--.
In Column 7, Line 3, delete "a diverter orifice and a".
In Column 7, Line 3, replace "diverter rotatably" with "A diverter is rotatably".
In Column 7, Line 4, replace "and fluid tightly" with "and is fluid tightly".
In Column 7, Line 18, replace "first and third connector" with "first and third connectors".
In Column 7, Line 36, replace "mitomycin" with "Mitomycin".
In Column 7, Line 37, replace "gemcitabine" with "Gemcitabine".
In Column 8, Line 8, insert a --,-- after "lumen".
In Column 13, Line 46, replace "FIGS. 8 to 11" with "FIGS. 8 to 12".
In Column 13, Line 59, insert --the-- after "and".
In Column 13, Line 60, replace "is" with "are".
In Column 14, Line 37, replace ""FIG. 9" with "FIG. 10".
In Column 15, Line 37, replace "state" with "states".
In Column 19, Line 14, replace "FIGS. 8 and 10" with "FIGS. 8 and 9".
In Column 19, Line 39, replace "position" with "position shown in FIG. 10".

In the Claims

In Column 22, Line 45, replace "mitomycin" with "Mitomycin".

Signed and Sealed this
Tenth Day of May, 2022

Katherine Kelly Vidal
*Director of the United States Patent and Trademark Office*

In Column 22, Line 46, replace "gemcitabine" with "Gemcitabine".
In Column 25, Line 33, replace "mitomycin" with "Mitomycin".
In Column 25, Line 34, replace "gemcitabine" with "Gemcitabine".